United States Patent
Coldren

(10) Patent No.: US 6,349,106 B1
(45) Date of Patent: Feb. 19, 2002

(54) METHOD FOR CONVERTING AN OPTICAL WAVELENGTH USING A MONOLITHIC WAVELENGTH CONVERTER ASSEMBLY

(75) Inventor: Larry Coldren, Santa Barbara, CA (US)

(73) Assignee: Agility Communications, Inc., Santa Barbara, CA (US)

( * ) Notice: Subject to any disclaimer, the term of this patent is extended or adjusted under 35 U.S.C. 154(b) by 0 days.

(21) Appl. No.: 09/614,895

(22) Filed: Jul. 12, 2000

Related U.S. Application Data

(63) Continuation-in-part of application No. 09/614,377, filed on Jul. 12, 2000, and a continuation-in-part of application No. 09/614,665, filed on Jul. 12, 2000, and a continuation-in-part of application No. 09/614,865, filed on Jul. 12, 2000, and a continuation-in-part of application No. 09/614,378, filed on Jul. 12, 2000, and a continuation-in-part of application No. 09/614,376, filed on Jul. 12, 2000, and a continuation-in-part of application No. 09/614,674, filed on Jul. 12, 2000, and a continuation-in-part of application No. 09/614,195, filed on Jul. 12, 2000, and a continuation-in-part of application No. 09/614,375, filed on Jul. 12, 2000, and a continuation-in-part of application No. 09/614,224, filed on Jul. 12, 2000.

(60) Provisional application No. 60/152,072, filed on Sep. 2, 1999, provisional application No. 60/152,049, filed on Sep. 2, 1999, and provisional application No. 60/152,038, filed on Sep. 2, 1999.

(51) Int. Cl.$^7$ ................................................ H01S 3/19
(52) U.S. Cl. ............................ 372/50; 372/32; 372/26
(58) Field of Search ............................ 372/50, 32, 26, 372/38.01

(56) References Cited

U.S. PATENT DOCUMENTS

| | | | |
|---|---|---|---|
| 5,088,105 A | 2/1992 | Scifres et al. ................. | 372/92 |
| 5,479,539 A | 12/1995 | Goldsmith et al. ............ | 385/14 |
| 5,525,541 A | 6/1996 | Krauz et al. ................. | 437/161 |
| 5,625,636 A | 4/1997 | Bryan et al. .................. | 372/50 |
| 5,674,778 A | 10/1997 | Lee et al. ..................... | 437/126 |
| 5,715,268 A | 2/1998 | Lang et al. .................... | 372/50 |
| 5,742,045 A | 4/1998 | Parker et al. ................ | 250/214 |

FOREIGN PATENT DOCUMENTS

| | | | |
|---|---|---|---|
| EP | 1 539 028 | 1/1979 | ............. H01S/3/02 |
| EP | 0 620 475 A1 | 3/1994 | ............ G02F/1/313 |

OTHER PUBLICATIONS

Bar–Chaim et al; "Monolithic Optoelectronic Integration of a GaAlAs laser, a field–effect transistor, and a photodiode"; App;. Phys. Lett. 44 (10) May 15, 1984.*

Bar–Chaim, N. et al., "Monolithic Optoelectronic Integration of a GaAIAs Laser, a Field–Effect Transistor, and a Photodiode", *Applied Physics Letters, US, American Institute of Physics*, May 15, 1984, vol. 44, No. 10, pp. 941–943.

(List continued on next page.)

*Primary Examiner*—Leon Scott, Jr.
(74) *Attorney, Agent, or Firm*—Paul Davis; Wilson Sonsini Goodrich & Rosati

(57) ABSTRACT

A method of converting an optical wavelength includes providing a wavelength converter assembly with a photodetector and a laser that have a common epitaxial structure with areas of differing bandgap. The laser including a laser resonator. An optical input with a first wavelength is absorbed at the wavelength converter assembly. A first electrical signal is generated from the photodetector in response to the optical input. The first electrical signal is conditioned and produces a conditioned first electrical signal. A second electrical signal is generated from the conditioned first electrical signal. A laser output is generated from a gain medium of the laser at a second wavelength in response to the second electrical signal.

36 Claims, 7 Drawing Sheets

OTHER PUBLICATIONS

Koch, T.L., "Semiconductor Photonic Integrated Circuits", *IEEE Journal of Quantum Electronics*, Mar. 27, 1991, No. 3, pp. 641–653.

Byoung–Sung, K. et al., "Dynamic Analysis of Widely Tunable Laser Diodes Integrated with Sampled–and–Chirped–Grating Distributed Bragg Reflectors and an Electroabsorption Modulator", *IEICE Trans Electron*, Aug. 1998, vol. E81–C, No. 8, pp. 1342–1349.

San–Liang, L. et al., "Sampled Grating DBR Laser Arrays with Adjustable 0.8/1.6–nm Wavelength Spacing", *IEEE Photonics Technology Letters*, Aug. 1999, vol. 11, No. 8, pp. 955–957.

Jayaraman, V. et al., "Theory, Design, and Performance of Extended Tuning Range Semiconductor Lasers with Sampled Gratings", *IEEE Journal of Quantum Electronics*, Jun. 29, 1993, vol. 29, No. 6, pp. 1824–1834.

* cited by examiner

US 6,349,106 B1

METHOD FOR CONVERTING AN OPTICAL WAVELENGTH USING A MONOLITHIC WAVELENGTH CONVERTER ASSEMBLY

CROSS-REFERENCE TO RELATED APPLICATION

This application is a continuation in part and claims the benefit of priority of U.S. Provisional Application Ser. No. 60/152,072, filed Sep. 2, 1999, U.S. Provisional Application Ser. No. 60/152,049, filed Sep. 2, 1999, U.S. Provisional Application Ser. No. 60/152,038, filed Sep. 2, 1999, which applications are fully incorporated by reference herein. This application is also continuation-in-part Ser. No. 09/614,377 filed Jul. 12, 2000 which claims benefit of No. 60/152 049 filed Sep. 2, 1999 and claims benefit of Prov. No. 60/152,038 filed Sep. 2, 1999 and a con't-in-part of U.S. Ser. Nos. 09/614,665, 09/614,865, 09/614,378, 09/614,376, 09/614,674, 09/614,195, 09/614,375, and 09/614,224, all filed on the same date as this application Ser. No. Jul. 12, 2000, which applications are fully incorporated by reference herein.

BACKGROUND OF THE INVENTION

1. Field of the Invention

This invention relates to wavelength converters of the type desirable in certain wavelength division multiplexed optical communication networks, as well as other applications where it is desirable to change the wavelength of the optical carrier of a modulated lightwave, and more particularly to optoelectronic wavelength converters in which an incoming lightwave having a first wavelength is detected by a photodetector that produces an electrical signal that in turn modulates a source of an outgoing lightwave having a desired second wavelength.

2. Description of the Related Art

Optoelectronic wavelength conversion processes have used as separate photodetectors, receiver and regeneration circuits, transmitter and driver circuits, and directly or externally modulated lasers. S. J. B. Yoo, "Wavelength conversion technologies for WDM network applications," *J. Lightwave Techn.* 14 (6) (June, 1996). These discrete-component wavelength converters have tended to be relatively bulky and expensive to manufacture. Also, the lasers generally have a fixed wavelength or a very limited tuning range.

There is a need for a monolithic wavelength converter assembly that provides for the process of detection and regeneration at some other wavelength. There is a need for a monolithic wavelength converter assembly fabricated on one semiconductor substrate using compatible photonic integrated circuit technology for all components. There is a further need for a wavelength converter assembly where signal amplification is obtained without the use of electronic transistors. There is yet a further need for a wavelength converter assembly where conditioning of the signal is done in combination with the detection or modulation process in the optical or electrical domain. There is still a further need for a wavelength converter assembly that has a wide tuning range and all of the components are fabricated on one semiconductor substrate using compatible photonic integrated circuit technology.

SUMMARY OF THE INVENTION

Figure 1:
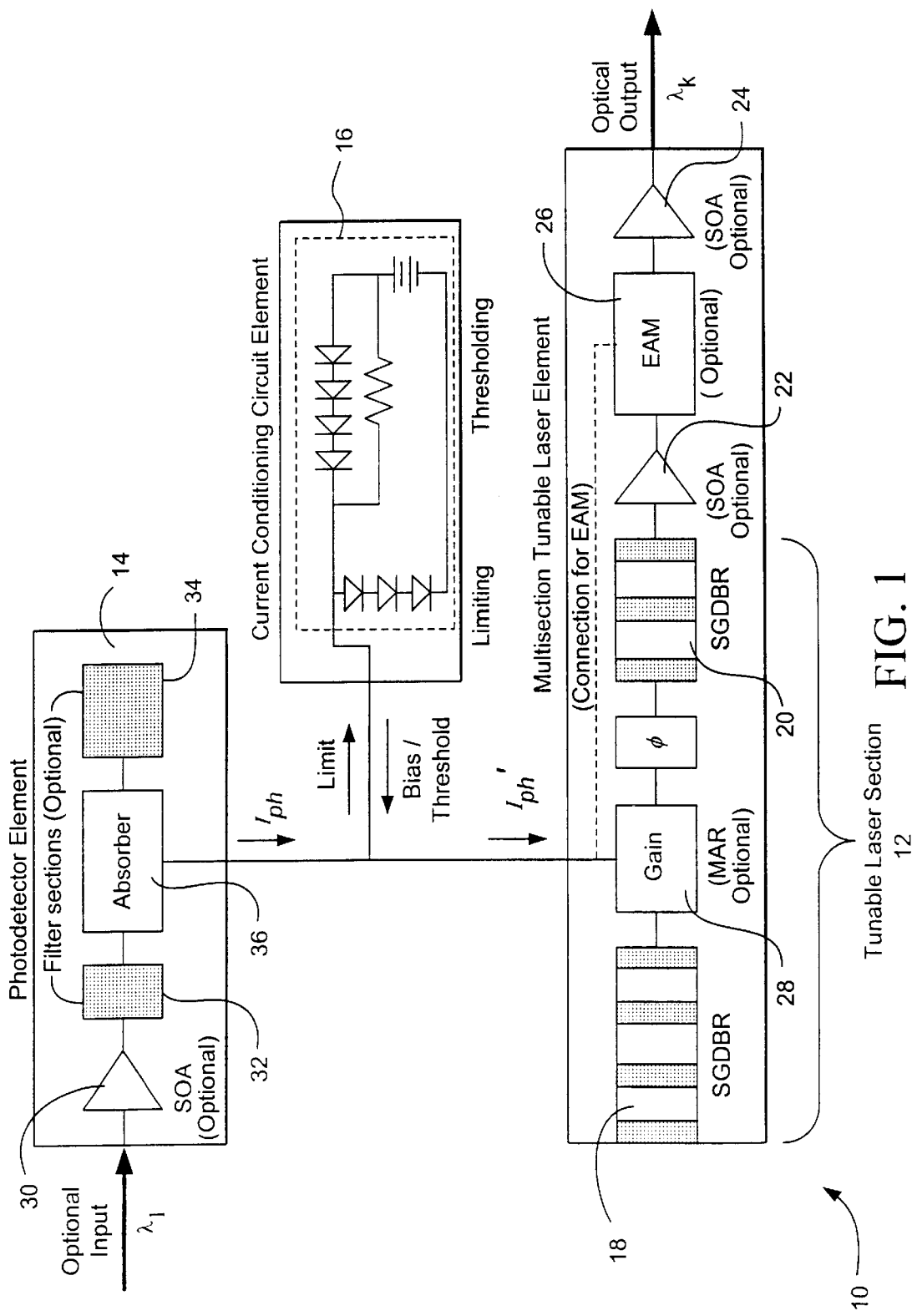
FIG. 1 is a block diagram of one embodiment of a wavelength converter assembly of the present invention.

Accordingly, an object of the present invention is to provide an improved wavelength converter assembly.

Another object of the present invention is to provide monolithic wavelength converter assembly that provides for the process of detection and regeneration at some other wavelength.

A further object of the present invention is to provide a monolithic wavelength converter assembly fabricated on one semiconductor substrate using compatible photonic integrated circuit technology for all components.

Yet another object of the present invention is to provide a wavelength converter assembly where signal amplification is obtained without the use of electronic transistors.

Another object of the present invention is to provide a wavelength converter assembly where conditioning of the signal is done in combination with the detection or modulation process in the optical or electrical domain.

A further object of the present invention is to provide a wavelength converter assembly that has a wide tuning range and all of the components are fabricated on one semiconductor substrate using compatible photonic integrated circuit technology.

Yet a further object of the present invention is to provide a monolithic wavelength converter assembly that provides high data bandwidths.

Another object of the present invention is to provide a monolithic wavelength converter assembly that provides a large output optical signal amplitude without the need for integrated transistors for electronic amplification.

Still a further object of the present invention is to provide a monolithic wavelength converter assembly that provides conditioned output data waveforms with lower noise and distortion than at an input.

Another object of the present invention is to provide a monolithic wavelength converter assembly that can be extended to large arrays of wavelength converters integrated on one substrate with photonic integrated circuit technology.

These and other objects of the present invention are achieved in a wavelength converter assembly that includes a substrate. An epitaxial structure is formed on the substrate with areas of different optical properties. A laser and a photodetector are formed in the epitaxial structure. The photodetector generates a first electrical signal in response to an optical signal. A conditioning circuit is coupled to the laser and the photodetector. The conditioning circuit receives the first electrical signal and provides a second electrical signal to the laser to modulate its optical output.

In another embodiment of the present invention, a wavelength converter assembly includes first and second semiconductor layers formed in an epitaxial structure. The first and second semiconductor layers having different dopings. A first waveguide layer is formed between the first and second semiconductor layers. The first waveguide layer includes first and second reflectors that define a resonant cavity. An optically active gain medium is disposed between the first and second reflectors. A photodetector is formed on the first semiconductor layer and includes an optically active absorber region. The photodetector generates a first electrical signal in response to an optical input.

DETAILED DESCRIPTION

Referring now to FIG. 1, a wavelength converter assembly 10 of the present invention provides for the process of detection and regeneration at some other wavelength to be carried out with a monolithic apparatus. Wavelength converter assembly 10 is fabricated on one semiconductor substrate using compatible photonic integrated circuit (IC) technology for all components. An advantage of wavelength converter assembly 10 over other devices is that signal amplification is obtained without the use of electronic transistors, which would involve incompatible fabrication technology. Moreover, the conditioning of the signal may be done in combination with the detection or modulation process in the optical or electrical domain. Laser output from wavelength converter assembly 10 can have a wide tuning range so that a large number of output wavelengths are possible.

In one embodiment, the elements of wavelength converter assembly 10 are fabricated on a single wafer. The various elements are derived from a common epitaxial layer structure, and are fabricated by common process steps.

Monolithic integration of optically dissimilar elements is accomplished by a method of fabrication that tailors optical properties of selected regions to a desired electro-optic function. Tailored optical properties, including the band gap, result in optically active and passive regions on the same wafer beginning from a common epitaxial layer structure. Further, the common fabrication process steps required for forming the apparatus elements are compatible with photonic device fabrication processes presently used in the lightwave industry. Thus, wavelength converter assembly 10 is readily manufacturable.

In a particular embodiment, the fabrication methods to selectively tailor the band gaps of regions of the wafer of wavelength converter assembly 10 include the steps of, implantation of impurities by low energy ions (less than about 200 eV) in a portion of a selected wafer region near the wafer surface; and annealing the wafer. This allows the impurities and vacancies implanted near the wafer surface to diffuse throughout the selected region and tailor the region's band gap to a desired electro-optic function.

For example, in the passive waveguide regions of the phase shift and mirror sections of a tunable laser element 12, the effective bandgap should be somewhat larger (e.g., >0.1 eV) than the operating lightwave energy, which is only slightly larger (typically ~0.01–0.05 eV) than the effective bandgap of the active layers in the gain section. Integrated external modulator elements may have sections with the same larger bandgap as the other passive regions, or a bandgap intermediate between that of the active and passive sections for some desired functionality such as chirp reduction or improved-linearity. Integrated external amplifier elements (M. J. O'Mahony, "Semiconductor laser Optical Amplifiers for Use in Future Fiber Systems," *J. Lightwave Techn.* 6 (4) (April, 1988.); A. E. Kelly, I. F. Lealman, L. J. Rivers, S. D. Perrin, and M. Silver, "Low noise figure (7.2 dB) and high gain (29 dB) semiconductor optical amplifier with a single layer AR coating," Electron. Lett., 33 pp 536–8 (1997.)) may have the same bandgap as the active gain section or a slightly modified bandgap for some functionality, such as increased saturation power or improved chirp of modulator/amplifier combinations. Robert G. Walker, "High-Speed III–V Semiconductor Intensity Modulators," *IEEE J Quant. Electron.*, 27, (3), 654–667, (March 1991); F. Koyama and K. Iga, "Frequency Chirping in External Modulators," *J. Lightwave Tech.*, 6 (1), 87–93, (January 1998).

In various embodiments of the present invention, the passive regions are created by selective removal of the lowest bandgap layers responsible for gain in the active regions within the same sequence as some other processing steps, such as grating formation in the mirror regions, are being carried out. B. Mason, G. A. Fish, S. P. DenBaars, and L. A. Coldren, "Widely Tunable Sampled Grating DBR Laser with Integrated Electroabsorption Modulator," *Photon. Tech. Letts.*, 11, (6), 638–640, (June 1999). In such cases the ion-implantation process is not necessary, but it may be utilized to better tailor other regions such as in integrated modulators and/or amplifier elements. This sequence is followed by a regrowth of the upper cladding layers required for the top portion of the optical waveguide.

According to aspects of the present invention, the data signal is available in electrical form for monitoring, tapping, and modification. In particular, a packet address or header information can be read and used to determine the routing of the information either by selection of the output wavelength or by setting the state of some switch that might follow the wavelength converter assembly. These and other desirable features are all incorporated within novel, monolithically-integrated optoelectronic wavelength converter assembly structures that make use of a manufacturable, integrated photonic IC technology. G. A. Fish, B. Mason, L. A. Coldren, and S. P. DenBaars, "Compact 1.55 µm Spot-Size Converters for Photonic Integrated Circuits," *Integrated Photonics Research* '99, Santa Barbara, Calif., paper no. RWD4, 375–377, (July 19–21, 1999).

Further features of wavelength converter assembly 10 include but are not limited to,: 1.) providing higher data bandwidths than currently available from currently available devices (T. Ido, S. Tanaka, M. Suzuki, M. Koizumi, H. Sano, and H. Inoue, "Ultra-High-Speed Multiple-Quantum-Well Electro-Absorption Optical Modulators with Integrated Waveguides," *J. Lightwave Techn.*, 14, (9), 2026–2034, (September 1996)), 2) providing a wider range of possible output wavelengths than currently available devices (V. Jayaraman, A. Mathur, L. A. Coldren and P. D. Dapkus, "Theory, Design, and Performance of Extended Tuning Range in Sampled Grating DBR Lasers," *IEEE J. Quantum Elec.*, 29, (6), 1824–1834, (June 1993)), 3.) providing equal or larger output optical signal amplitude than current devices without the need for integrated transistors for electronic amplification (J. K. Kim, E. Hall, O. Sjölund, and L. A. Coldren, "Epitaxially-Stacked Multiple-Active-Region 1.55 µm Lasers for Increased Differential Efficiency," *Appl. Phys. Letts.*, 74, (22) 3251–3253, (May 31, 1999); J. T. Getty, O. Buchinsky, R. A. Slavatore, B. Mason, P. G. Piva, S. Charbonneau, K. S. Grabowski, and L. A. Coldren, "Monolithic Series-Connected 1.55 µm Segmented-Ridge Lasers," *Electronics Letters*, 35, (15), 1257–1258, (July 22, 1999)), 4.) providing conditioned output data waveforms having lower noise and distortion than at the input and 5.) providing capabilities for extensions to large arrays of such wavelength converters, the arrays integrated on one substrate with existing photonic IC technology. Coldren, L., "Diode Lasers and Photonic Integrated Circuits," Wiley, (1995).

FIG. 1 illustrates certain generic elements, in block diagram form, of wavelength converter assembly 10. Illustrated are a multisection tunable laser element 12 (hereafter referred to as "laser 12"), a photodetector element 14 (hereafter referred to as "photodetector 14" and a current conditioning circuit element 16. The insets in the blocks are suggestive of the possible contents of elements 12, 14 and 16. Current from photodetector 14 modulates the laser 12 after being conditioned by the conditioning circuit. The net functionality provides wavelength conversion of an optical carrier modulated with some data such that: i) an arbitrary output wavelength within a band can be emitted; ii) the amplitude of the output can be adjusted within a useful range; and, iii) the noise and distortion on the data can be reduced. An important aspect of the invention is integration with a common photonic IC technology that has been described in F. Koyama and K. Iga, "Frequency Chirping in External Modulators," *J. Lightwave Tech.*, 6 (1), 87–93, (January 1998); B. Mason, G. A. Fish, S. P. DenBaars, and L. A. Coldren, "Widely Tunable Sampled Grating DBR Laser with Integrated Electroabsorption Modulator," *Photon. Tech. Letts.*, 11, (6), 638–640, (June 1999). Moreover, integration of elements 12, 14 and 16 provides an advantageous functionality that is not possible by interconnecting discrete elements using conventional printed circuit board or multi-chip module technology. Additionally, integration of elements 12, 14 and 16 enables low-cost, high-yield manufacturing processes to used.

As illustrated in FIG. 1, laser 12 can include first and second SGDBR's 18 and 20, a first and second SOA's 22 and 24 and EAM 26 and a multiple active region, MAR 28. Photodetector element 16 can include an SOA 30, first and second filters 32 and 34 and an absorber 36.

Figure 2A:
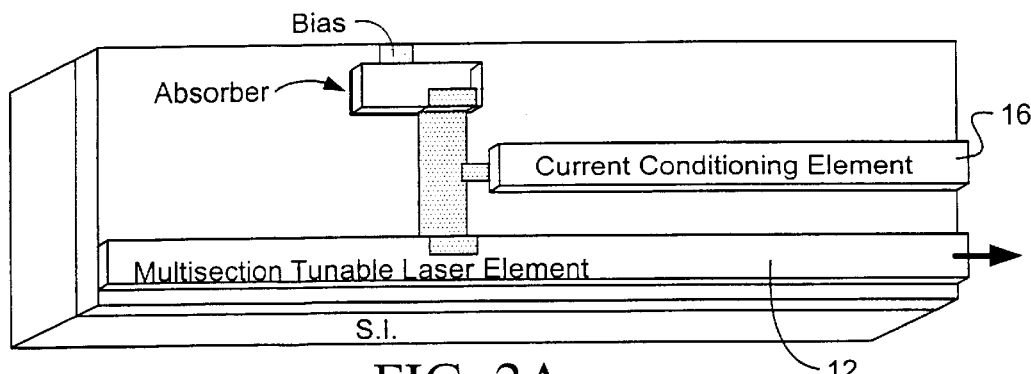
FIG. 2(a) is a top down schematic view of a waveguide photodetector that can be part of the FIG. 1 wavelength converter assembly.

Wavelength converter 10 offers a number of advantages. In the embodiment illustrated in FIG. 2(a), the surface-illuminated geometry photodetector 14 enables efficient and polarization independent coupling of light from optical fibers to absorber 36 of photodiode 12. Moreover. it does not require a large footprint on the substrate. and its modest dimensions, in one embodiment approximately 10–30 µm in diameter, provide for high bandwidth, sensitive operation. In various embodiments, the sensitivity of wavelength converter assembly 10 can be enhanced by incorporation of a multi-layer reflective stack beneath the wavelength converter assembly 10 to create a resonant-cavity photodiode 14. This stack forms the lower cladding region of laser 12 without any complication. As in other embodiments, surface-illuminated photodiode 14 is isolated by a proton and/or He+ ion implantation or other means well known to those skilled in the art, rendering the surrounding areas semi-insulating. In particular embodiments, the bottom contact of wavelength converter assembly 10 is brought out to the side for biasing and the top contact is directly interconnected to laser 12 with a shunt branch to conditioning circuit 16.

Figure 2B:
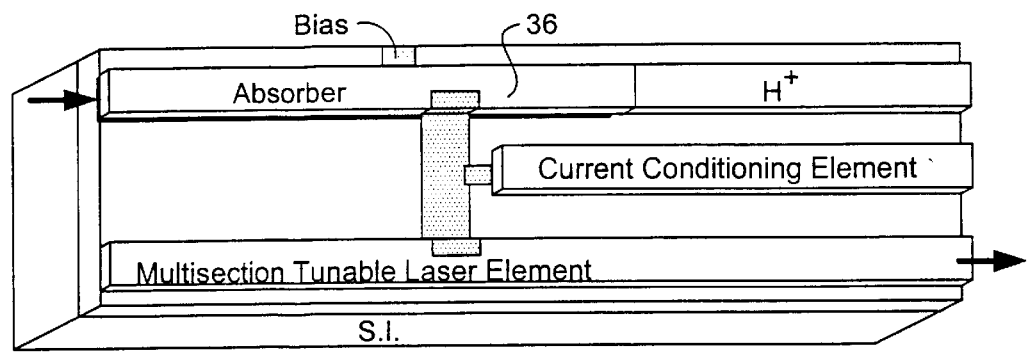
FIG. 2(b) is a top down schematic view of a waveguide photodetector that can be part of the FIG. 1 wavelength converter assembly.

A waveguide layer structure of photodetector 14 illustrated is FIG. 2(b) is identical to the gain section of laser 12. In this embodiment, the waveguide layer structure of photodetector 14 provides for higher saturation power than typical surface-illuminated designs. Optical coupling to the waveguide can be enhanced by the integration of compatible mode transformers using techniques such as those described in G. A. Fish, B. Mason, L. A. Coldren, and S. P. DenBaars, "Compact 1.55 µm Spot-Size Converters for Photonic Integrated Circuits," *Integrated Photonics Research* '99, Santa Barbara, Calif., paper no. RWD4, 375–377, (July 19–21, 1999). For ultra high bandwidth embodiments, such as for example greater than 50 GHz, a terminated traveling wave electrode structure may be incorporated. A suitable traveling wave electrode structure is described in 8. T. Ido, S. Tanaka, M. Suzuki, M. Koizumi, H. Sano, and H. Inoue, "Ultra-High-Speed Multiple-Quantum-Well Electro-Absorption Optical Modulators with Integrated Waveguides," *J. Lightwave Techn.*, 14, (9), 2026–2034, (September 1996).

Figure 2C:
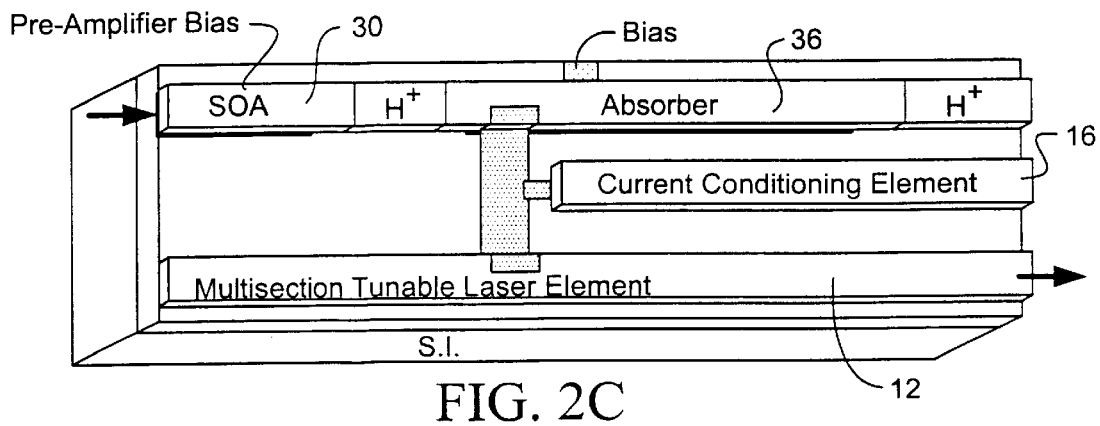
FIG. 2(c) is a top down schematic view of waveguide photodetector integrated with a semiconductor-optical amplifier ("SOA") preamplifier that can be part of the FIG. 1 wavelength converter assembly.

Referring now to FIG. 2(c), the addition of an optical preamplifier, SOA 30, increases the optical signal incident on absorber section 36 and provides higher output photocurrent. This is advantageous by allowing the use of low-level data while still obtaining sufficient current to properly modulate laser 12 and also allows for data regeneration by a shunt conditioning circuit. SOA 30 can also provide for signal level adjustment in conjunction with an external control circuit. Noise added by SOA 30 may be removed by current conditioning circuit 18, resulting in a noise figure that does not degrade the data. The layer structure of SOA 30 can be identical to the gain section of laser 12.

Figure 2D:
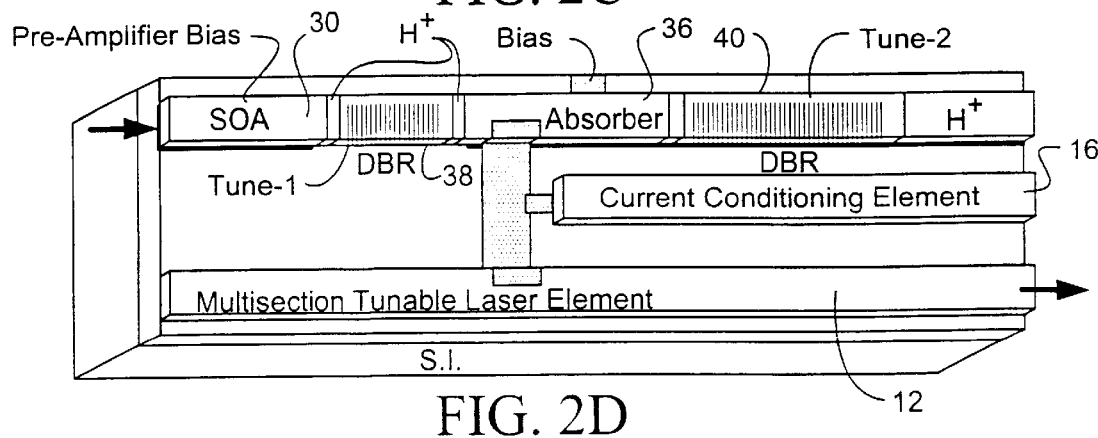
FIG. 2(d) is a top down schematic view of a waveguide photodetector integrated with a SOA preamplifier and a tunable resonant-cavity filter that can be part of the FIG. 1 wavelength converter assembly.

If the signal to noise level is low, or if unwanted data at another wavelength is present in the input lightwave, or if a shorter absorber section is desired, it may be advantageous to place absorber 36 within a resonant cavity to filter out unwanted signals out-of-band. As illustrated in FIG. 2(d), photodetector 14 is integrated with SOA 30 and a tunable resonant-cavity filter. This waveguide geometry reflects light signals that are not within the resonant bandwidth of the resonant cavity formed by two DBR's 38 and 40 and enhances the signal. A shorter absorber length may be used for total absorption and high quantum efficiency. This shortened length, in turn, reduces photodetector's 14 capacitance, enabling very high bandwidth operation.

Figure 3A:
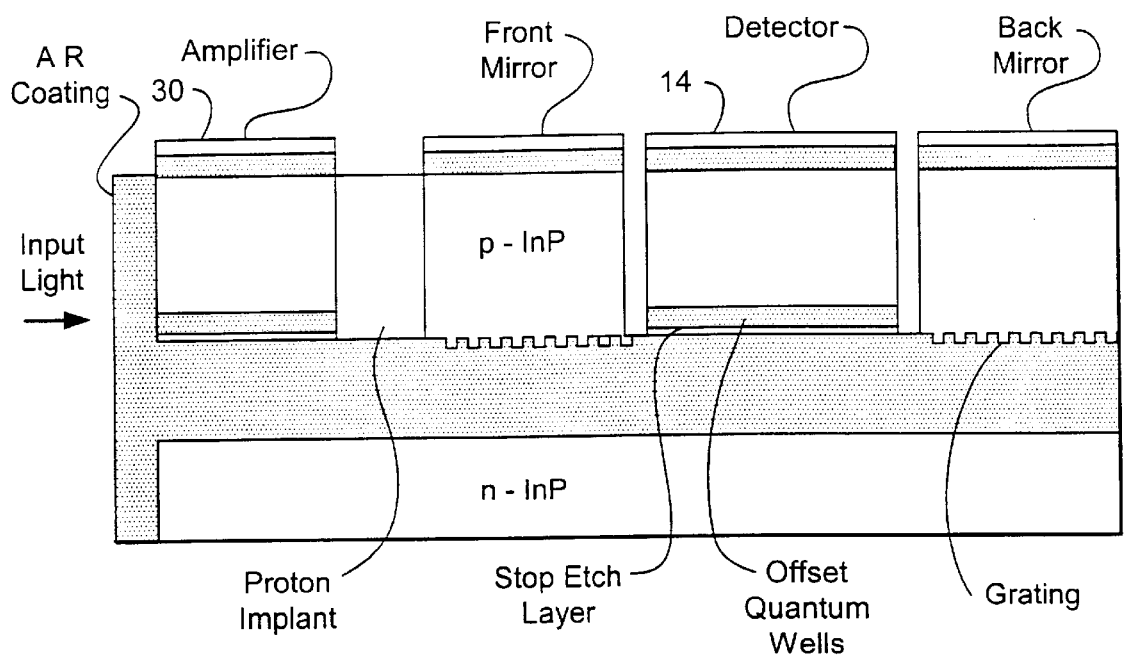
FIG. 3(a) is a cross sectional view of the semiconductor layer structure of the FIG. 2(d) assembly in which passive sections are created by removal of the active regions prior to regrowth.
Figure 3B:
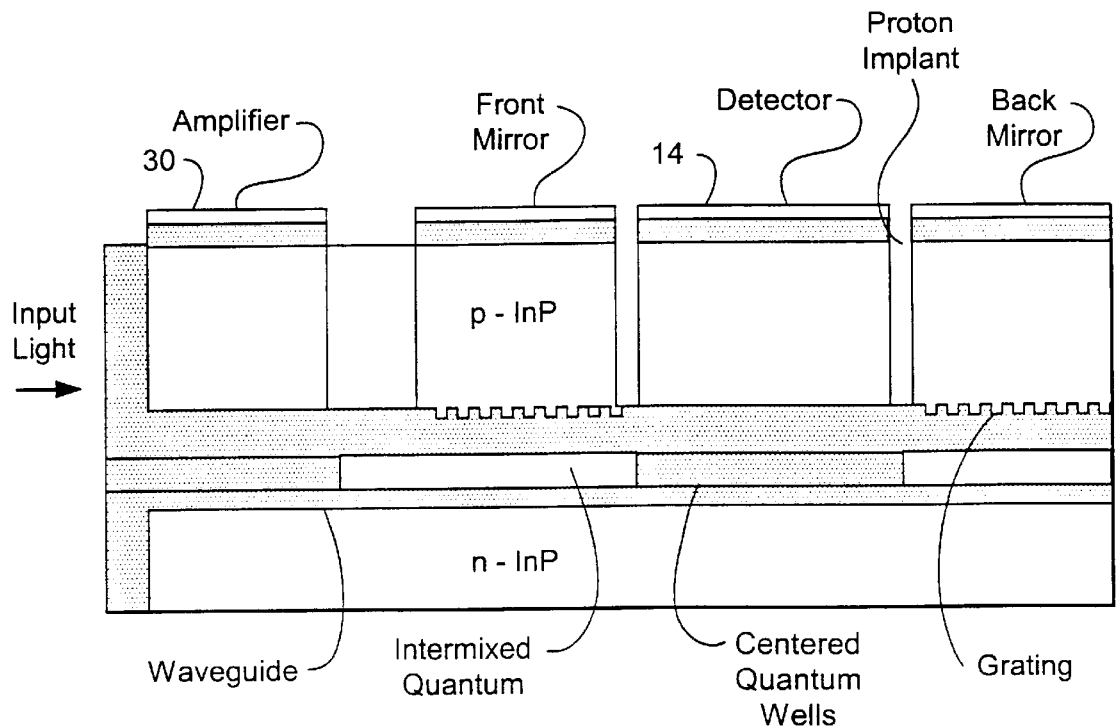
FIG. 3(b) is a cross sectional view of the semiconductor layer structure of the FIG. 2(d) assembly in which passive sections are created by variable thickness and composition quantum-wells via intermixing after uniform growth or selective area growth.

FIGS. 3(a) and 3(b) are cross-sectional views of the semiconductor layer waveguide structure of the FIG. 2(d) photodetector 14. In FIG. 3(a) passive sections are created by removal of the active regions prior to regrowth. In FIG. 3(b) passive sections are created by variable thickness and composition quantum-wells via intermixing after uniform growth or selective area growth. FIG. 3(a) and 3(b) illustrate that waveguide photodetectors 14 are compatible with the tunable sections of laser 12 that are illustrated in FIG. 5. It will be appreciated that various sections shown in FIGS. 3(a) and 3(b) are omitted in the FIG. 2(a), 2(b) and 2(c) embodiments.

Figure 4A:
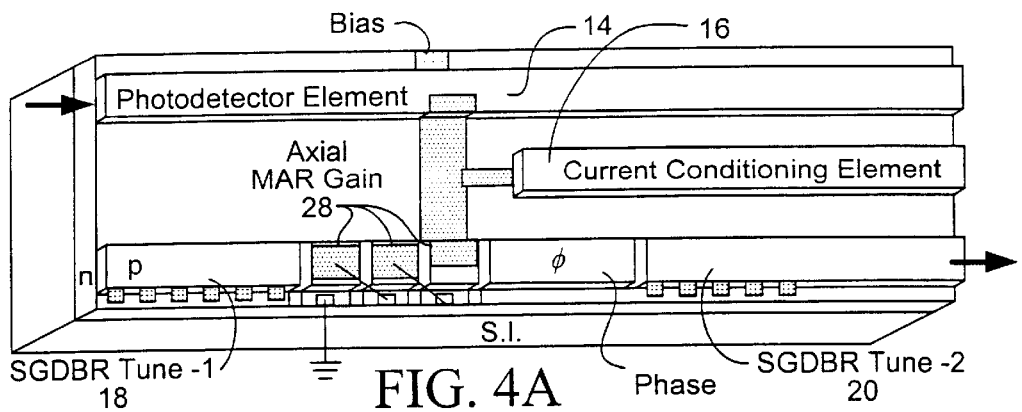
FIG. 4(a) is a schematic top down view of a sampled-grating distributed-Bragg-reflector ("SGDBR") tunable laser having a series-connected, axially segmented multiple-active region that can be part of the FIG. 1 wavelength converter assembly.
Figure 5A:
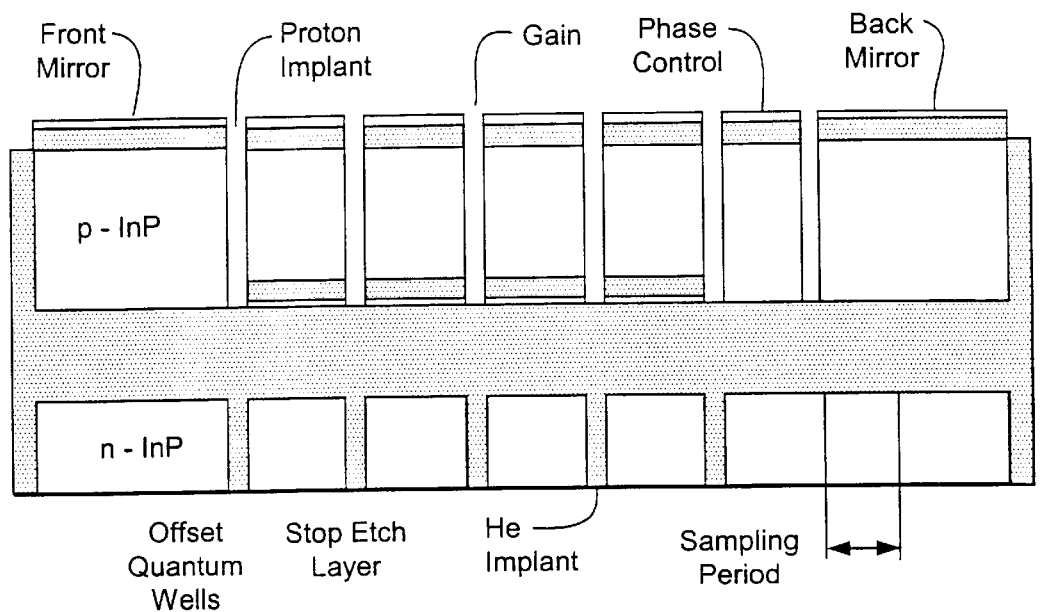
FIG. 5(a) is a cross sectional view of the FIG. 4(a) structure.

FIGS. 4(a) and 5(a) illustrate embodiments of wavelength converter assembly 10 with a series-connected, axially segmented active region that obtains signal gain within a widely tunable SGDBR laser 12 as described in U.S. Pat. No. 4,896,325. The principle of operation of each SGDBR 18 and 20 is well known to those skilled in the art, as is the concept of using MAR 28 within a single optical cavity to obtain a differential efficiency greater than unity.

Figure 4B:
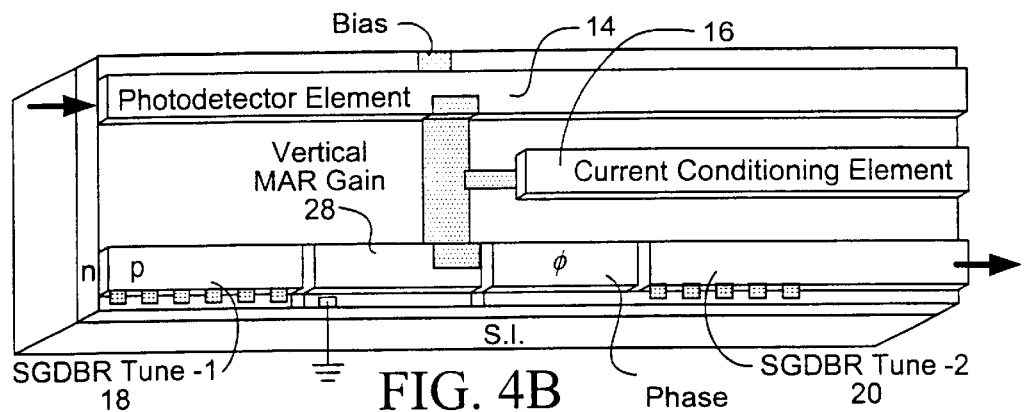
FIG. 4(b) is a schematic of a SGDBR tunable laser that has a series-connected, vertically stacked multiple-active region that can be part of the FIG. 1 wavelength converter assembly.
Figure 5B:
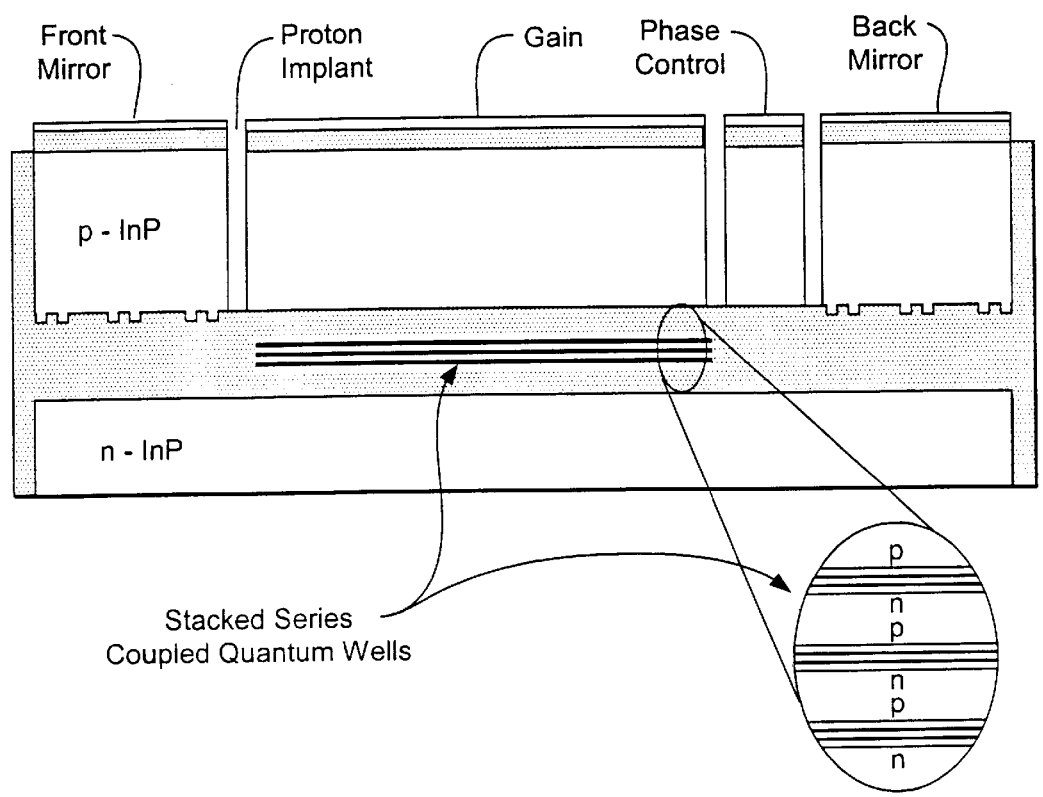
FIG. 5(b) is a cross sectional view of the FIG. 4(b) structure.

FIGS. 4(b) and 5(b) illustrate another embodiment employing the same concepts. In this embodiment, the separate pin active regions of the gain section are integrated vertically with the series electrical connections derived from intermediate n$^+$-p$^+$tunnel diodes. This layer structure is particularly useful in combination with the vertical resonant-cavity photodiode embodiment of FIG. 2(a), since more absorption can lead to photodiodes with broader optical bandwidth and better efficiency as well. Absorbers can be placed at standing wave peaks and the tunnel diodes at standing wave nulls to provide a multiplication in absorbency by nearly 2× the number of active regions.

Figure 4C:
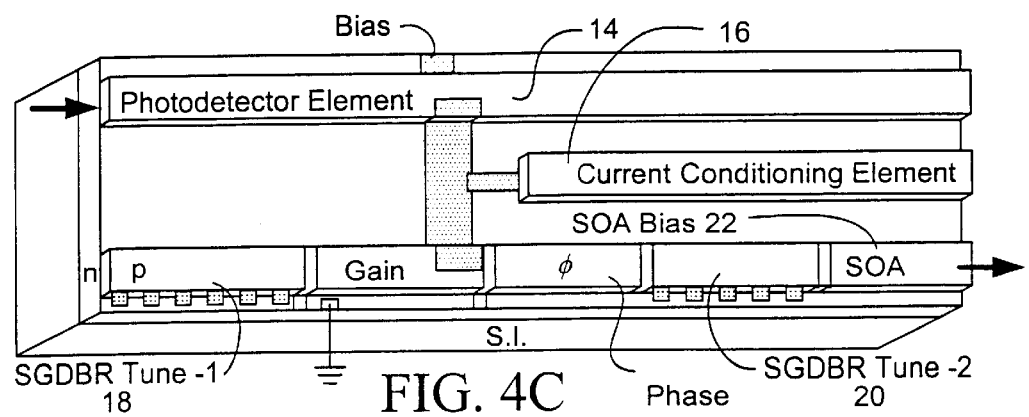
FIG. 4(c) is a schematic top down view of a SGDBR tunable laser with an integrated external SOA that can be part of the FIG. 1 wavelength converter assembly.

FIG. 4(c) illustrates another embodiment of the invention. In FIG. 4(c), the signal gain is enhanced relative to other embodiments by the addition of integrated SOA 22 external to the laser cavity. The data signal current is still applied to the gain section, and the gain section may either be of a conventional single active region, or MAR 28, as in FIG. 4(a) or 4(b) embodiments, for more signal gain. External SOA 22 can provide about 20 dB of gain, whereas the multiple active region design provides for roughly unity gain. Normal lasers have differential efficiencies ~20–30%; thus the MAR 28 design gives about 3 to 5× enhancement. The MAR 28 design is advantageous because it does not degrade the signal-to-noise ratio, whereas SOA 22 does. However, if the signal level is already high, as it can be with a MAR gain section and/or gain in photodetector 14, the constant noise added by SOA 22 can be negligible. This geometry also allows for the leveling of the output data signal level via an external control circuit.

Figure 4D:
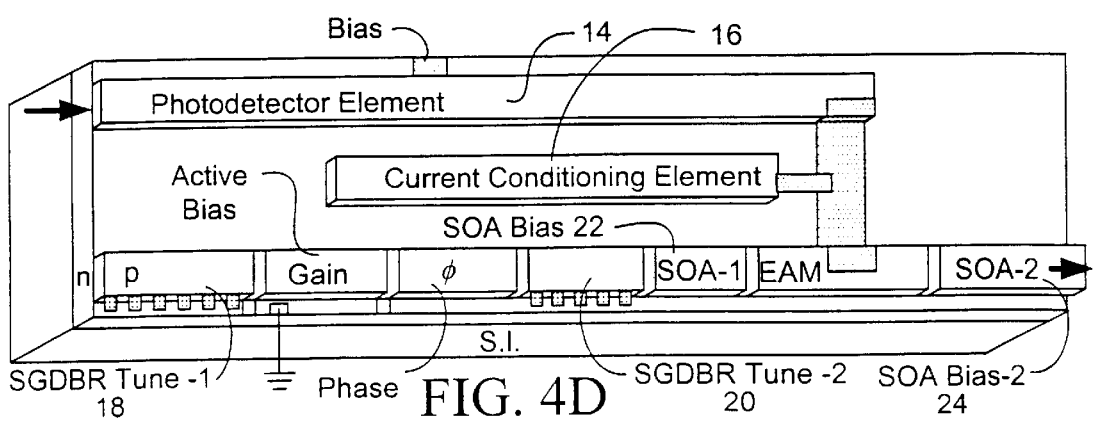
FIG. 4(d) is a schematic top down view of a SGDBR tunable laser with an integrated external electro-absorption modulator (EAM) and two SOAs that can be part of the FIG. 1 wavelength converter assembly.

If the signal bandwidth is very high, such as but not limited to 15 GHz or greater, direct modulation of laser 12 may be difficult. Also, if chirping of the wavelength is a problem, direct modulation may not be an optimal solution. Finally, if the output wavelength of laser 12 must be set very accurately, direct modulation may compromise the ability of control circuit 16 to hold the wavelength with sufficient accuracy. For all of these reasons, use of external modulation, such as illustrated in FIG. 4(d), may be desired. In this case, the data signal current is applied to the integrated external modulator. An EAM 44 is shown, but an interferometric modulator, such as a Mach-Zehender or directional coupler modulator or other equivalent, is also possible by using passive waveguide sections of appropriate design. As indicated, SOA's 22 and 24 may also be advantageously employed to increase the input carrier level and output modulated data. Use of MAR 28 actives may also be advantageous if laser RIN is to be minimized. Since the active region can be biased by a high-impedance source in this case, no low-source-impedance high-frequency signal, the inherent noise on laser 12 output can be reduced to sub-shot noise levels. SOA's 22 and 24 at laser's 12 output can be avoided by accomplishing the desired signal gain in photodetector 14 where their noise may be removed by the current conditioning circuit. This provides for signal gain, with a maximal signal-to-noise ratio.

Figure 7:
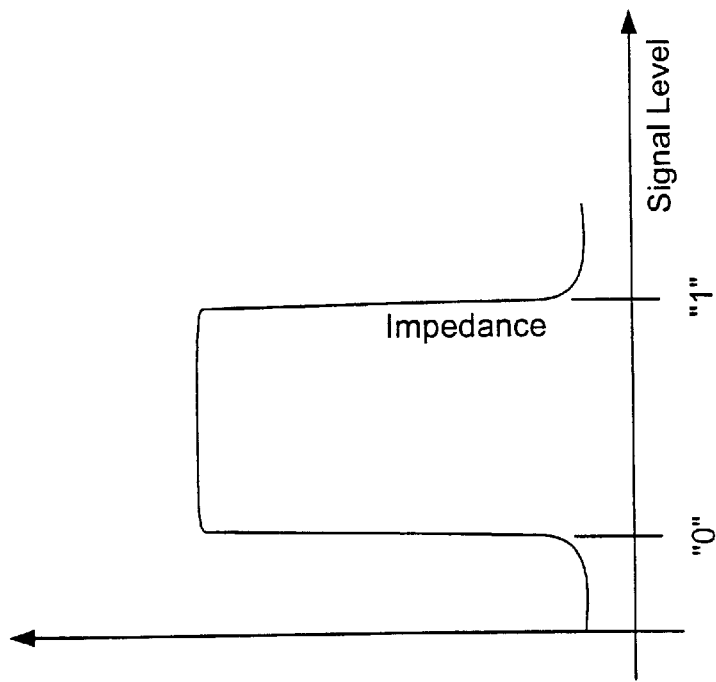
FIG. 7 is a plot of the desired impedance of the FIG. 1 nonlinear current conditioning circuit.

In many embodiments, the current conditioning circuit 16 can be easily created in Si-CMOS if external shunting circuits are used. However, for high-speed operation, the packaging may not provide sufficiently low shunt capacitance, so at least some of the functionality may be desirable to have on-chip. The shunt impedance of this circuit is shown in FIG. 7. With this circuit shunting the drive current, noise on the baseline (logical '0') and maximum (logical '1') of the data can be removed, provided that the signal level can be adjusted to the appropriate levels by the gain components in photodetector 14.

Figure 6:
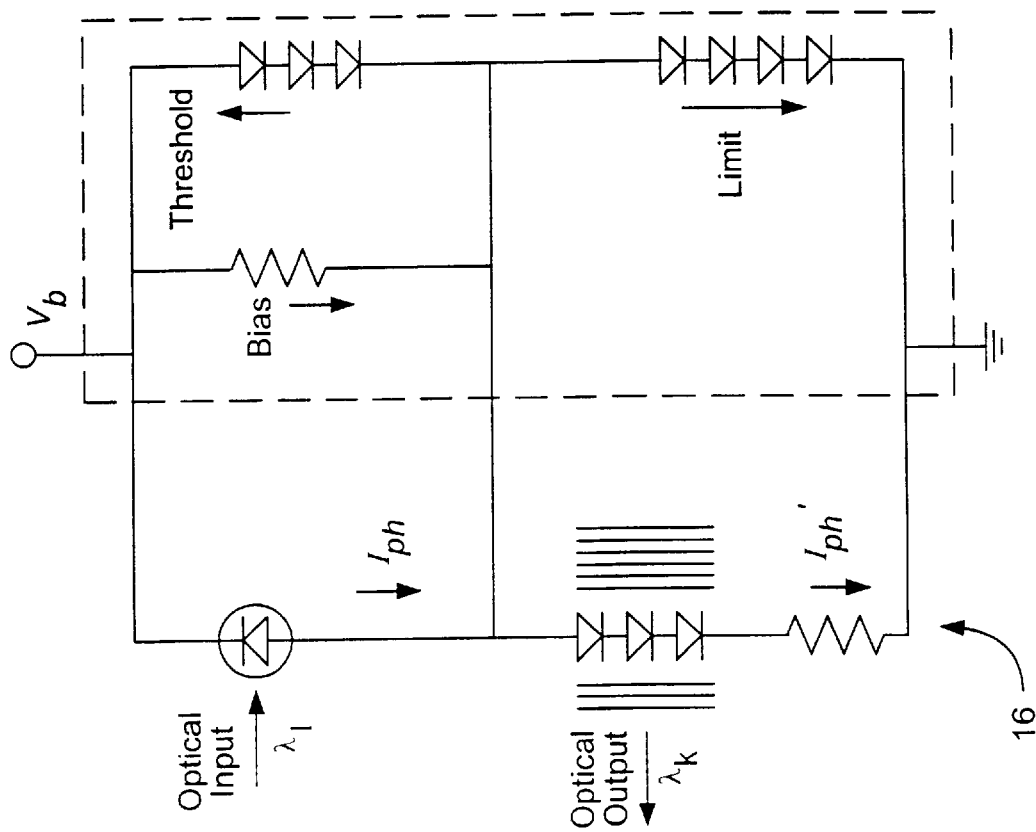
FIG. 6 is schematic diagram of an equivalent circuit that can be used with the structures of FIGS. 2(a), 2(b), 4(a) and 4(b) as well as an integrable current conditioning circuit.

One embodiment of an integrable conditioning circuit 16 for the laser bias is shown in FIG. 6. Diode chains can be used to threshold and limit the level of the modulating data signal. These can be integrated using the same fabrication steps already necessary to create photodetector 14 and tunable elements of laser 12 shown in FIGS. 2 through 5.

Other conditioning circuits are possible that provide the characteristic of FIG. 7 and the desired laser active region (gain) or EAM bias using compatible integrable technology, and these can be obtained by using standard circuit design packages. If the photocurrent is to be applied to the EAM, such as may be desired for high-speed operation, then current conditioning circuit 16 may supply the correct reverse bias voltage to the EAM for some desired operation. Such desired operations include but are not limited to minimizing the chirp or maximizing the linearity for an output wavelength from laser 12.

Wavelength converter assembly 10 is a monolithically integrated opto-electronic wavelength converter assembly. Particular embodiments comprise: photodetector 14 electrically coupled to a multi-section, laser 12 having a differential efficiency greater than unity, where the photocurrent can be conditioned by a circuit element to provide tapping, thresholding, and limiting of the detected data. Key elements of circuit conditioning circuit 16 can be integrable with the same fabrication steps required for photodetector 14 and laser 12.

In certain embodiments, photodetector 14 is an edge-illuminated waveguide photodetector. In other embodiments, photodetector 14 is a surface-illuminated element. In the waveguide embodiments, SOA 30 may be integrated with photodetector 14 using the same fabrication sequence for additional gain or level control. In these embodiments, tunable waveguide filter 42 may also be incorporated with the same fabrication sequence to filter out unwanted signals or noise from SOA 30.

Laser 12 can use SGDBR's 18 and 20 and gain and phase-shift sections to provide for output wavelength tunability over a range of several tens of nanometers. To accomplish net signal gain, the gain section of laser 12 may contain several active regions that are driven electrically in series, and/or laser 12 may incorporate an integrated external SOA at its output port.

In a particular embodiment, the conditioned photocurrent is connected to an integrated external modulator to provide reduced wavelength chirping and generally enable higher data rate operation than feasible with direct modulation of the gain section of laser 12. Electro-absorption modulators (EAMs) (Robert G. Walker, "High-Speed III–V Semiconductor Intensity Modulators," *IEEE J. Quant. Electron.*, 27, (3), 654–667, (March 1991); F. Koyama and K. Iga, "Frequency Chirping in External Modulators," *J. Lightwave Tech.*, 6 (1), 87–93, (January 1998); B. Mason, G. A. Fish, S. P. DenBaars, and L. A. Coldren, "Widely Tunable Sampled Grating DBR Laser with Integrated Electroabsorption Modulator," *Photon. Tech. Letts.*, 11, (6), 638–640, (June 1999)) or interferometric modulators can be integrated within the same fabrication sequence as the other elements. In this particular embodiment, SOA sections precede and/or follow the modulator section to accomplish net signal gain and/or data level adjustment. In addition, the combined dispersion characteristics of the SOAs and EAM can be used to provide a desired net chirp characteristic.

In other embodiments, current conditioning circuit element 16 is non-linear and consists of a connection to an external source to supply laser 12 with a necessary threshold current. In another embodiment, current conditioning circuit 16 includes a microwave filter to remove subcarrier header information. In still another embodiment, current conditioning circuit 16 can comprise a limiting circuit to shunt off any currents above a given level. Current conditioning circuit element 16 can also comprise a thresholding circuit to shunt away photocurrent below a given level. These latter circuits may be partially external to the monolithic photonic IC, or they may comprise appropriate series diode chains that can be compatibly integrated.

All or some of the elements of wavelength converter assembly 10 can be created with a standardized photonic IC fabrication processes. Thus, various options can be added dependant only upon the desired specifications and without the need to develop a new or incompatible materials growth and device fabrication sequence. In one specific embodiment, wavelength converter assembly 10 includes elements that are based on InP substrates, which can provide wavelength conversion and other functionality near the 1.55 μm wavelength band. It will be appreciated that wavelength converter assembly 10 can use other material platforms.

Figure 8A:
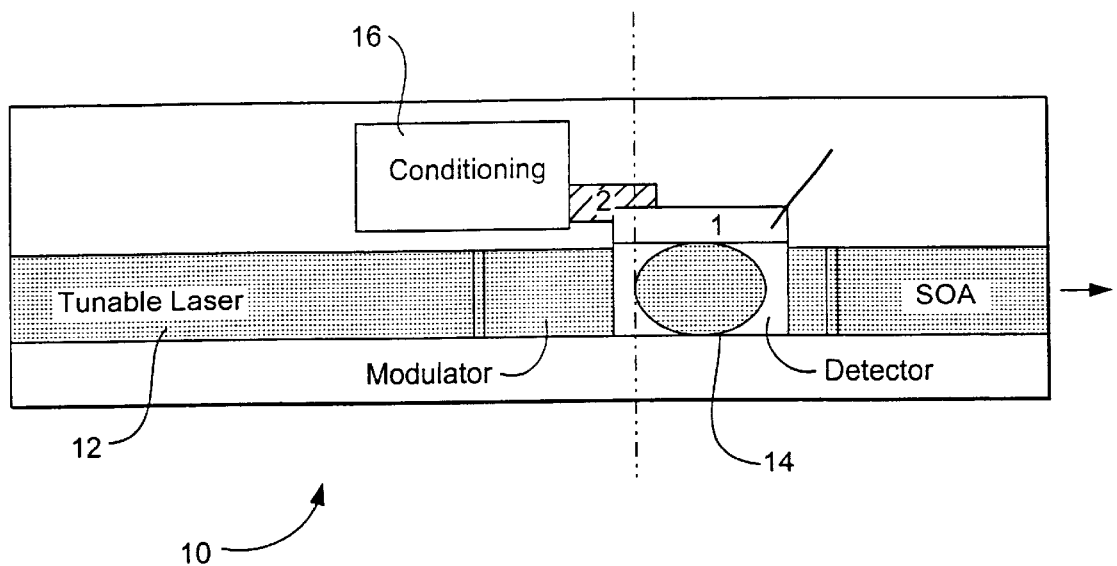
FIGS. 8(a) and (b) illustrate an embodiment of a monolithic wavelength converter assembly of the present invention where the photodetector is integrated directly on top of the laser.
Figure 8B:
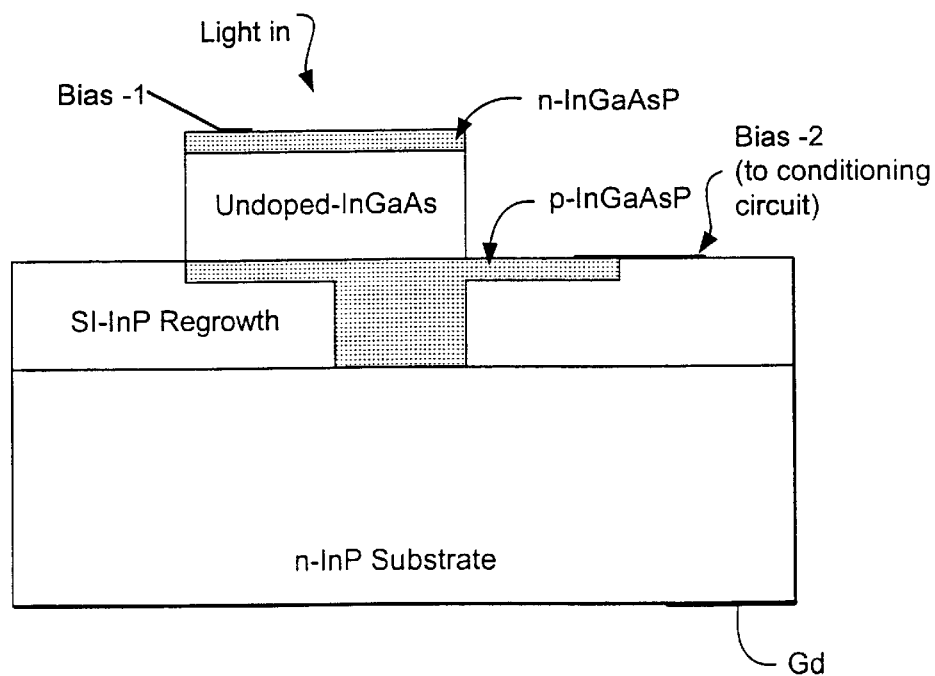

Another embodiment of wavelength converter assembly 10 is illustrated in FIGS. 8(*a*) and (*b*). In this embodiment, metal interconnects between photodetector 14 and laser 12 are avoided by integrating photodetector 14 directly on top of laser 12. This eliminates any excess series resistance or inductance or shunt capacitance between the input and output stages and optimizes the configuration for high-data rate operation. Semi-insulating regrowth of a buried-heterostructure waveguide is also illustrated for high-speed operation. Current conditioning circuit 16 can also be connected by contacting to the intermediate p-InGaAsP layer between vertically stacked photodetector 14 and laser 12. As illustrated, the connection is directly to the integrated modulator, which can be the preferred connection for high-speed low-chirp operation. Vertical illumination is also illustrated, but a horizontal waveguide detector configuration is also possible. The vertical configuration may be preferred since there is less crosstalk between input and output lightwave signals. Such vertical integration is obtained by performing several regrowth steps as is common in such photonic integrated circuits using techniques well known to those skilled in the art.

In one mode of operation of the FIGS. 8(*a*) and (*b*) embodiment, a reverse bias voltage is applied between bias-1 and bias-2 electrodes to deplete the InGaAs absorber region and provide minimal sweep out times for photocarriers. Bias-2 would is set to the voltage appropriate for optimal operation of the modulator. Example dc potentials include but are not limited to, −2 V on bias-2 electrode and −6 V on bias-1 electrode. The thickness of the InGaAs absorber is adjusted to be sufficient to absorb most of the incoming light but not so thick as to slow the transit of carriers to the contact layers. It will be appreciated that an avalanche photodetector (APD) may also be used in place of the simple pin detector indicated in FIGS. 8(*a*) and (*b*). In this case additional layers are desired to optimize the gain-bandwidth product of the APD.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method of converting an optical wavelength, comprising:

providing a wavelength converter assembly with a photodetector and a laser with a common epitaxial structure with areas of differing bandgap, the laser including a laser resonator;

absorbing an optical input having a first wavelength at the wavelength converter assembly;

generating a first electrical signal from the photodetector in response to the optical input;

conditioning the first electrical signal and produce a conditioned first electrical signal;

generating a second electrical signal from the conditioned first electrical signal;

generating a laser output from a gain medium of the laser at a second wavelength in response to the second electrical signal.

2. The method of claim 1, wherein the wavelength converter assembly includes a current conditioning circuit coupled to the photodetector and the laser.

3. The method of claim 2, wherein the current conditioning circuit conditions the first electrical signal and produces the conditioned first electrical signal.

4. The method of claim 3, wherein the conditioning circuit contains nonlinear circuit elements to limit a magnitude of the second electrical signal wherein a maxima of signal pulses are reshaped.

5. The method of claim 3, wherein the conditioning circuit contains nonlinear circuit elements to supply a minimum level to the second electrical signal wherein a minima of signal pulses are reshaped.

6. The method of claim 5, wherein the substrate is semi-insulating InP.

7. The method of claim 3, further comprising:

supplying a minimum level to the second electrical signal; and reshaping a minima of signal pulses.

8. The method of claim 3, wherein the current conditioning circuit provides bias voltages to the photodetector and laser.

9. The method of claim 1, wherein conditioning the first electrical signal includes modifying the first electrical signal's bias and threshold.

10. The method of claim 1, wherein the optical input is absorbed at the photodetector and a gain from the gain medium occur at the common epitaxial structure.

11. The method of claim 1, wherein the optical input is absorbed at the photodetector and a gain from the gain medium occur at a common level of the common epitaxial structure.

12. The method of claim 1, further comprising:
controlling a phase of the laser output.

13. The method of claim 1, wherein the laser has a first reflector and a second reflector that define the laser resonator, wherein at least one of the first and second reflectors is frequency selective and tunable.

14. The method of claim 13, further comprising:
tuning a maximum reflectivity of the first reflector relative to a maximum reflectivity of the second reflector to select the second wavelength.

15. The method of claim 1, further comprising:
modulating the laser output.

16. The method of claim 1, wherein the second electrical signal modulates the laser's output.

17. The method of claim 1, further comprising:
selecting a range of wavelengths for detection at the photodetector.

18. The method of claim 1, further comprising:
amplifying the optical input prior to absorption by the wavelength converter assembly.

19. The method of claim 1, wherein the second electrical signal modulates the laser's output.

20. A method of converting an optical wavelength, comprising:
providing a wavelength converter assembly having an epitaxial structure with areas of differing bandgap that includes a waveguide layer positioned between first and second semiconductor layers of the epitaxial structure, an optically active gain medium positioned between first and second reflectors that define a resonant cavity, and a photodetector;
detecting an optical input at the photodetector; and
generating a laser output from the wavelength converter assembly in response to the optical input.

21. The method of claim 20, wherein the laser output is modulated outside the laser resonator at the common epitaxial structure.

22. The method of claim 20, wherein the optical input has a first wavelength.

23. The method of claim 22, further comprising:
generating a first electrical signal from the photodetector in response to the optical input.

24. The method of claim 23, further comprising:
conditioning the first electrical signal and produce a conditioned first electrical signal.

25. The method of claim 24, wherein the wavelength converter assembly includes a current conditioning circuit coupled to the photodetector and the laser.

26. The method of claim 25, wherein the current conditioning circuit conditions the first electrical signal and produces the conditioned first electrical signal.

27. The method of claim 24, further comprising:
generating a second electrical signal from the conditioned first electrical signal.

28. The method of claim 27, further comprising:
providing bias voltages to the photodetector and laser.

29. The method of claim 27, further comprising:
limiting a magnitude of the second electrical signal; and
reshaping a maxima of signal pulses.

30. The method of claim 27, further comprising:
generating the laser output from a gain medium of the laser at a second wavelength in response to the second electrical signal.

31. The method of claim 20, further comprising:
controlling a phase of the laser output.

32. The method of claim 20, further comprising:
tuning a maximum reflectivity of the first reflector relative to a maximum reflectivity of the second reflector to select the laser output.

33. The method of claim 20, further comprising:
modulating the laser output.

34. The method of claim 33, wherein the laser output is modulated outside the resonant cavity at the common epitaxial structure.

35. The method of claim 20, further comprising:
selecting a range of wavelengths for detection at the photodetector.

36. The method of claim 20, further comprising:
amplifying the optical input prior to prior to detecting the optical input.

* * * * *